United States Patent
Kolomeyer et al.

(10) Patent No.: US 7,851,660 B1
(45) Date of Patent: Dec. 14, 2010

(54) PROCESS FOR MAKING PERILLYL ALCOHOL

(75) Inventors: Gennadiy G. Kolomeyer, Jacksonville, FL (US); Douglas A. Ferone, Jacksonville, FL (US)

(73) Assignee: Millennium Specialty Chemicals, Inc., Houston, TX (US)

( * ) Notice: Subject to any disclaimer, the term of this patent is extended or adjusted under 35 U.S.C. 154(b) by 0 days.

(21) Appl. No.: 12/799,118

(22) Filed: Apr. 19, 2010

(51) Int. Cl.
*C07C 35/18* (2006.01)

(52) U.S. Cl. ...................................... 568/826; 568/827

(58) Field of Classification Search ................. 568/826, 568/827
See application file for complete search history.

(56) References Cited

U.S. PATENT DOCUMENTS

| | | |
|---|---|---|
| 3,925,485 A | 12/1975 | Chabardes et al. |
| 3,956,404 A | 5/1976 | Walling et al. |
| 3,957,856 A | 5/1976 | Ansari et al. |
| 3,993,604 A | 11/1976 | Thomas et al. |
| 4,254,291 A | 3/1981 | Kane |
| 4,306,099 A | 12/1981 | Fetizon et al. |
| 5,994,598 A | 11/1999 | Chastain et al. |
| 6,835,686 B2 | 12/2004 | Kolomeyer et al. |

OTHER PUBLICATIONS

U.S. Appl. No. 12/799,119, filed Apr. 19, 2010, Kolomeyer et al.
Bessiere, Y. et al., "Isomerization of Limonene Epoxides, Allylic Rearrangement of p-Metntha-1(7),8-dien-2-ols: Preparation of Perilla Alcohol," *Journal of Chemical Research* (S), 1977, 304-305.
Tius, M., et al., "A Convenient Synthesis of (R)-(+)-Perillaldehyde," *Synthetic Communications, 18*, (16&17), 1905-1911, (1988).

*Primary Examiner*—Sikarl A Witherspoon
(74) *Attorney, Agent, or Firm*—Jonathan L. Schuchardt

(57) ABSTRACT

A process for making perillyl alcohol is disclosed. The process comprises isomerizing a starting material comprising trans-isocarveol at a temperature within the range of 100° C. to 220° C. in the presence of a Group 5 metal catalyst to produce perillyl alcohol. We surprisingly found that trans-isocarveol, which can be selectively produced from a commercially available mixture of cis- and trans-LMO, can be isomerized directly to perillyl alcohol. Yields of perillyl alcohol are improved when the isomerization is performed under an inert atmosphere and/or in the presence of a phenolic antioxidant. Performing the isomerization in the presence of a high-boiling alcohol and/or distilling the perillyl alcohol product from the reaction mixture in the presence of a high-boiling alcohol, enhances yields and maximizes catalyst use. The resulting distillation residue, which contains recovered Group 5 metal catalyst, is valuable for catalyzing additional trans-isocarveol isomerizations.

14 Claims, No Drawings

PROCESS FOR MAKING PERILLYL ALCOHOL

FIELD OF THE INVENTION

The invention relates to a process for making perillyl alcohol, an intermediate useful in the flavor and fragrance industry.

BACKGROUND OF THE INVENTION

Perillyl alcohol, a terpene, occurs naturally and has antimicrobial and anticancer properties. Hydrogenation of perillyl alcohol provides 4-isopropyl cyclohexanemethanol, which is a valuable fragrance ingredient having a fresh, clean odor reminiscent of white petals and flower blossoms.

Synthetic approaches to perillyl alcohol have been reviewed (see U.S. Pat. Nos. 3,993,604 and 5,994,598) and fall into three groups. In a first approach, a terpene hydrocarbon (α-pinene, β-pinene, or limonene) is oxidized using an equimolar amount of a toxic or explosive reagent (benzoyl peroxide, lead tetraacetate, or selenium dioxide). U.S. Pat. No. 3,956,404, which uses benzoyl peroxide, is illustrative.

A second approach prepares perillyl alcohol by isomerizing β-pinene oxide (see, e.g., U.S. Pat. Nos. 3,993,604; 4,306,099; and 5,994,598). These methods use an acidic catalyst, give low yields of the desired alcohol, and generate a large amount of wastewater. They often produce mixtures of isomers resulting from double bond migrations, and the by-products are difficult to remove. Some of the methods produce disubstituted derivatives that require an additional step to convert them to perillyl alcohol.

In yet another approach, 1,2-limonene monoxide (hereinafter "LMO" or "limonene oxide") is used as the starting material. A mixture of cis- and trans-LMO is isomerized to produce, respectively, trans-isocarveol and cis-isocarveol:

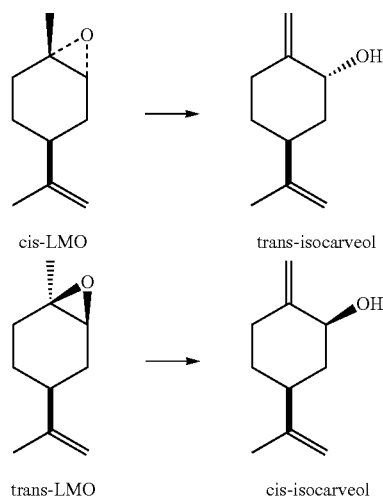

The isocarveols are converted into ester or other derivatives that are in turn isomerized to perillyl alcohol derivatives. Finally, the perillyl alcohol derivatives are hydrolyzed to produce perillyl alcohol. For examples of this approach, see U.S. Pat. Nos. 3,993,604 and 3,957,856; *Synth. Commun.* 18 (1988) 1905, and *J. Chem. Research* (S) (1977) 304. Interestingly, the latter reference indicates that the isocarveols cannot be isomerized directly to perillyl alcohol, which is consistent with our failure to find any reference teaching such a direct isomerization.

Although a mixture of cis- and trans-limonene oxide is readily available as a starting material, the need to derivatize isocarveols and subsequently remove the ester or other protecting group undermines the value of the third approach. Ideally, perillyl alcohol could be produced directly from the isocarveols in a commercially viable process.

Assuming that such a direct isomerization is even possible, which isocarveol isomer, cis- or trans-, is the better starting material? Distillation is impractical for separating cis- and trans-LMO, and commercially available limonene oxide contains 50-65% of cis-LMO and 35-50% of trans-LMO. If one isocarveol isomer is, in fact, better than the other for making perillyl alcohol, how can the preferred isomer be made selectively from a mixture of cis- and trans-LMO?

In U.S. Pat. No. 6,835,686, we described a method for isomerizing a mixture of cis- and trans-LMO to give isocarveols (compound 3). See, in particular, Example 45, which utilizes 1.7 wt. % of chromium octoate catalyst, 0.5 wt. % of a phenolic activator, and reflux at greater than 220° C. for 2.5 hours such that conversion of the combined mixture of LMO isomers exceeds 99.5% (see Table 2 of the '686 patent). No information is provided about the relative amounts of trans- and cis-isocarveols obtained; however, a high conversion of both cis- and trans-LMO to the isocarveols is evident from the overall quantitative conversion.

Numerous processes are known for isomerizing allylic alcohols. One such process uses a Group 5 metal catalyst such as ammonium metavanadate to ($NH_4VO_3$) or the like to effect the transformation (see, e.g., U.S. Pat. Nos. 3,925,485 and 4,254,291). Known processes of this type, however, typically involve isomerization of open-chain tertiary allylic alcohols to secondary and primary alcohols. The reaction has not been applied to cyclic, secondary alcohols such as cis- and trans-isocarveol.

SUMMARY OF THE INVENTION

The invention is a process for making perillyl alcohol. The process comprises isomerizing a starting material comprising trans-isocarveol at a temperature within the range of 100° C. to 220° C. in the presence of a Group 5 metal catalyst to produce perillyl alcohol. We surprisingly found that trans-isocarveol, which can be selectively produced from a commercially available mixture of cis- and trans-limonene oxide (see copending application Ser. No. 12/799,119, filed Apr. 19, 2010, can be isomerized directly to perillyl alcohol, thereby obviating the need to derivatize isocarveols and subsequently deprotect a perillyl alcohol precursor. Yields of perillyl alcohol are improved, and formation of high-molecular-weight by-products is minimized, when the isomerization is performed under an inert atmosphere and/or in the presence of a phenolic antioxidant. We also found that performing the isomerization in the presence of a high-boiling alcohol and/or distilling the perillyl alcohol product from the reaction mixture in the presence of a high-boiling alcohol enhances yields and maximizes catalyst use. The resulting distillation residue, which contains recovered Group 5 metal catalyst, is valuable for catalyzing additional trans-isocarveol isomerizations.

DETAILED DESCRIPTION OF THE INVENTION

The inventive process comprises isomerizing a starting material comprising trans-isocarveol at a temperature within the range of 100° C. to 220° C. in the presence of a Group 5 metal catalyst to produce perillyl alcohol. Surprisingly, we found that trans-isocarveol can be isomerized directly to perillyl alcohol, thereby avoiding the need for additional synthetic steps, including the need to prepare a derivatized trans-isocarveol and to deprotect a perillyl alcohol precursor.

Because both cis- and trans-isocarveol can, in theory, isomerize to give perillyl alcohol, one might reasonably ask why trans-isocarveol is used in the inventive process. We found that the isocarveol isomers behave differently in the allylic isomerization. Both reactions are equilibrium controlled, and in the case of trans-isocarveol, the equilibrium is reached at a molar ratio of trans-isocarveol to perillyl alcohol of about 1:2. However, while trans-isocarveol reacts relatively quickly to give perillyl alcohol, the cis-isomer converts very slowly (see Example 1 and Table 1, below). Consequently, trans-isocarveol is the more favorable starting material for making perillyl alcohol.

The trans-isocarveol can be obtained from any source, but it is preferably made by selectively isomerizing a mixture, preferably a commercially available one, comprising cis-limonene oxide (cis-LMO) and trans-limonene oxide (trans-LMO) in the presence of a chromium catalyst and a phenolic modifier as we describe in copending application Ser. No. 12/799,119, filed Apr. 19, 2010. Selective conversion to predominantly the trans-isocarveol isomer is preferably accomplished by controlling a combination of factors, including temperature, reaction time, catalyst choice and amount, modifier choice and amount, and other considerations, as described in the above-mentioned application. Commercially available limonene oxide contains 50-65% of cis-LMO and 35-50% of trans-LMO.

Limonene oxide isomerization is preferably performed under conditions effective to convert more than 50% of the cis-LMO to trans-isocarveol and less than 50% of the trans-LMO to cis-isocarveol. We surprisingly found that cis-LMO isomerizes to trans-isocarveol more rapidly than trans-LMO isomerizes to cis-isocarveol. Our own earlier work (see, e.g., U.S. Pat. No. 6,835,686, Example 45) indicated no particular isomer preference in the LMO isomerization process using a chromium catalyst and phenolic modifier. However, by carefully controlling the isomerization conditions, we deduced that cis-LMO is actually the more reactive isomer. This finding, coupled with our discovery that direct isomerization of isocarveols to perillyl alcohol is possible and proceeds preferentially from trans-isocarveol, enable an overall efficient two-step conversion of cis-LMO to perillyl alcohol:

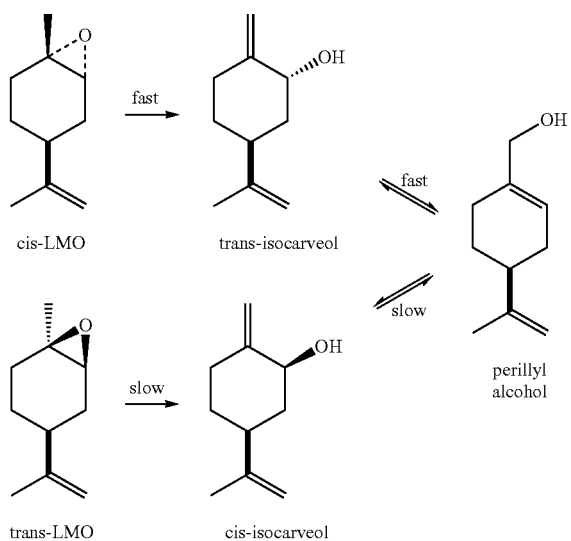

Thus, trans-isocarveol is the more preferred starting material for making perillyl alcohol, and any method that favors its generation relative to the amount of cis-isocarveol is desirable.

The purity level of the trans-isocarveol is usually not critical. As we demonstrate below in Example 1, trans-isocarveol can be successfully converted to perillyl alcohol in the presence of a substantial proportion of cis-isocarveol. Preferably, the starting material contains at least 50 wt. %, more preferably at least 60 wt. %, and most preferably at least 80 wt. % of trans-isocarveol. In addition to cis-isocarveol, the starting material may contain traces of carveols, LMO isomers, or other components. However, as we explained in application Ser. No. 12/799,119, very pure trans-isocarveol can be isolated from the selective LMO isomerization process using a single distillation. Such purified trans-isocarveol is preferred for making perillyl alcohol according to the inventive process, particularly if a pharmaceutical grade of perillyl alcohol is desired. For these and similar end uses, the starting material preferably contains at least 90 wt. %, more preferably at least 95 wt. %, and most preferably at least 99 wt. % of trans-isocarveol.

The direct allylic isomerization of trans-isocarveol to perillyl alcohol is performed in the presence of a Group 5 metal catalyst, preferably one comprising vanadium or niobium, more preferably vanadium. Suitable Group 5 metal catalysts include salts, organic esters, and complexes of Group 5 transition metals. Preferred catalysts include reaction products of a Group 5 metal compound with a high-boiling alcohol, preferably a primary or secondary alcohol, glycol, or polyol, as described below. Suitable catalysts are described, for example, in U.S. Pat. Nos. 3,925,485 and 4,254,291, the teachings of which are incorporated herein by reference. Useful catalysts include, for instance, ammonium metavanadate, ammonium metaniobate, ethyl orthovanadate, n-hexyl orthovanadate, tert-butyl orthovanadate, tert-amyl orthovanadate, trihexylorthovanadate, cyclohexyl orthovanadate, triethylene glycol orthovanadate, tetraethylene glycol orthovanadate, vanadyl acetylacetonate, and the like. Ammonium metavanadate is particularly preferred.

The amount of Group 5 metal catalyst used is from 15 ppm to 1.5 wt. % based on the amount of trans-isocarveol used. A more preferred range is from 100 to 5000 ppm, most preferably from 500 to 2000 ppm. The amount of catalyst actually used will depend on the reaction temperature, time, nature of the Group 5 metal catalyst, purity of the trans-isocarveol, and other factors, and is within the skilled person's discretion. Preferably, the amount of Group 5 metal catalyst used is kept to a minimum to avoid forming undesirable levels of high-molecular-weight by-products.

The reaction is performed under conditions effective to isomerize the trans-isocarveol to perillyl alcohol. This involves heating the trans-isocarveol and Group 5 metal catalyst at a temperature effective to cause the desired allylic rearrangement, i.e., at a temperature in the range of 100° C. to 220° C. More preferably, the temperature is from 130° C. to 190° C., and most preferably from 150° C. to 170° C.

As noted earlier, one process previously used to isomerize open-chain tertiary allylic alcohols (see U.S. Pat. Nos. 3,925,485 and 4,254,291) to primary or secondary alcohols involves a Group 5 metal-catalyzed direct isomerization. The absence of similar reports for directly converting trans-isocarveol (a cyclic, secondary alcohol) to perillyl alcohol combined with other literature recommending a more-laborious, indirect approach (via derivatization, isomerization, and deprotection) suggest that direct isomerization of trans-isocarveol is problematic. We surprisingly found that it is possible to directly isomerize trans-isocarveol to perillyl alcohol in good yields. We also found that the yield of perillyl alcohol can be enhanced by performing the isomerization using a minimum amount of catalyst and in the presence of a phenolic antioxidant and/or an inert atmosphere.

Preferably, a phenolic antioxidant is included in the process. Suitable phenolic antioxidants are well known. They include substituted or unsubstituted hydroquinones, dihydroxybenzenes, aminohydroxybenzenes, and the like, particularly alkyl-, amino-, and/or halo-substituted compounds. Specific examples include 2,6-di-tert-butyl-4-methylphenol (BHT); 4-hydroxymethyl-2,6-di-tert-butylphenol; 2,4-diaminophenol; 3-methyl-p-aminophenol; 4,6-diamino-2-methylphenol; p-methylaminophenol; p-(tert-butyl)catechol, p-(1,1-diethylpropyl)catechol, p-tributylmethylcatechol, tetrakis methylene(3,5-di-tert-butyl-4-hydroxyhydrocinnamate)methane, tert-butyl hydroquinone (TBHQ), and the like. A phenolic antioxidant precursor, i.e., a compound that can easily be converted into a phenolic antioxidant by contacting it with a reducing agent, can be used instead of or in addition to the phenolic antioxidant. Examples of such precursors include benzoquinones and naphthoquinones. Hindered phenolic antioxidants are particularly preferred. BHT and TBHQ are most preferred. Many suitable phenolic antioxidants are commercially available from suppliers such as, e.g., Ciba Specialty Chemicals, Chemtura, and Cytec.

The phenolic antioxidant (and/or precursor thereof) is preferably used in an amount effective to improve the yield of perillyl alcohol from trans-isocarveol compared with the yield obtained in the absence of the antioxidant. Preferably, the amount used will range from 10 to 5000 ppm, more preferably from 100 to 1000 ppm, and most preferably from 200 to 600 ppm, based on the amount of trans-isocarveol.

The process is preferably performed under an inert atmosphere comprising nitrogen, argon, helium, or the like, or their mixtures. When oxygen is not excluded, the yield of perillyl alcohol is generally lower (see Table 2).

The isomerization reaction mixture normally contains some unreacted trans-isocarveol, the desired perillyl alcohol product, impurities, and the Group 5 metal catalyst, which forms esters with some of the perillyl alcohol. The mixture is preferably warmed with dilute aqueous base, such as 5% aqueous sodium hydroxide solution, to hydrolyze these esters and liberate the perillyl alcohol. The Group 5 metal catalyst dissolves in the aqueous phase and is removed. The organic phase is then preferably neutralized, dried if desired, and fractionated, preferably at reduced pressure, to isolate the perillyl alcohol. Any trans-isocarveol recovered in this distillation can be recycled to the isomerization unit.

Perillyl alcohol recovered by distillation can be very pure, particularly if relatively pure trans-isocarveol is used as the starting material for the isomerization. Preferably, the perillyl alcohol is more than 95% pure, more preferably more than 99% pure, and most preferably more than 99.5% pure.

The process can provide perillyl alcohol having a high degree of optical purity. Other known processes, such as those that utilize β-pinene oxide as a starting material, are unable to provide perillyl alcohol with such high optical purity. Preferably, the perillyl alcohol has an optical rotation $[\alpha]_D^{22}$ of at least 100°, more preferably at least 103°, most preferably at least 104°.

The asymmetric center of LMO (at C4 of the cyclohexyl ring) retains its configuration in the isomerization to trans-isocarveol and in the subsequent conversion of trans-isocarveol to perillyl alcohol. Thus, e.g., R-(+)-limonene oxide gives R-(+)-isocarveol, and the configuration is also retained upon direct isomerization to give R-(+)-perillyl alcohol.

In one aspect of the invention, illustrated by Example 8, a high-boiling alcohol is included in the distillation used to recover trans-isocarveol and perillyl alcohol. The high-boiling alcohol effectively displaces perillyl alcohol and trans-isocarveol from their corresponding Group 5 metal esters, thereby facilitating removal of the valuable product and starting material from the reaction mixture by distillation. The distillation is conveniently performed at a low enough temperature (<145° C.) to recover the products while avoiding reverse isomerization of perillyl alcohol back to trans-isocarveol. The residue from this distillation contains the Group 5 metal catalyst in the form of an ester of the high-boiling alcohol mixed with an excess of the high-boiling alcohol. Thus, this aspect of the invention provides a way to recover and reuse the Group 5 metal catalyst, which would otherwise be lost in an aqueous wash phase.

As we show in Example 8, such a catalyst mixture can be reused for additional trans-isocarveol isomerizations. Thus, in another inventive aspect, the isomerization to give perillyl alcohol is performed in the presence of the high-boiling alcohol. Preferred high-boiling alcohols are alcohols, diols, and polyols having boiling points greater than 260° C. Primary and secondary alcohols are preferred. Suitable high-boiling alcohols include, for example, triethylene glycol, tetraethylene glycol, tripropylene glycol, and the like, and mixtures thereof.

The following examples merely illustrate the invention. Those skilled in the art will recognize many variations that are within the spirit of the invention and scope of the claims.

EXAMPLE 1

Preparation of Perillyl Alcohol from a Mixture of Cis- and Trans-Isocarveols

A mixture of cis- and trans-isocarveols (100 g, isomer wt. ratio shown in Table 1) and ammonium vanadate (0.4 g) is agitated and heated at 160° C. for 8 h under a nitrogen atmosphere. Samples taken at 2-h intervals starting at reaction time=4 hours are analyzed by gas chromatography to follow the progress of the reaction. Results appear in Table 1.

TABLE 1

| Conversion of Isocarveol Mixtures to Perillyl Alcohol versus Reaction Time | | | | |
|---|---|---|---|---|
| Reaction time (h) | 0 | 4 | 6 | 8 |
| trans-Isocarveol (wt. %) | 62.5 | 39.1 | 26.7 | 18.7 |
| cis-Isocarveol (wt. %) | 27.9 | 27.3 | 26.8 | 26.3 |
| Perillyl alcohol (wt. %) | 0 | 23.6 | 36.6 | 45.1 |

As shown in Table 1, trans-isocarveol is converted much more rapidly to perillyl alcohol than the cis-isomer. This experiment demonstrates: (1) that mixtures of cis- and trans-isocarveol can be directly isomerized to produce perillyl alcohol and (2) that trans-isocarveol is the preferred starting material for making perillyl alcohol.

EXAMPLE A

Preparation of Trans-Isocarveol

The procedure of U.S. Pat. No. 6,835,686 is generally followed, but with much less catalyst and less-stressed conditions. Thus, a mixture of limonene oxide (66% cis-, 34% trans-; 794 g), chromium octoate (12% Cr, product of Shepherd Chemicals, 0.53 g, 0.07 wt. %), and 2-aminophenol (0.66 g) is agitated and refluxed with a Dean-Stark trap for 1.5 h. The pot temperature at reflux increases from 198° C. to a maximum of 211° C. during the course of the reaction. After cooling, the reaction mixture is analyzed by gas chromatography. It contains: cis-LMO, 3.6% (95% conversion); trans-LMO, 29.7% (13% conversion), and trans-isocarveol, 51.3% (82% selectivity based on reacted cis-LMO). Fractionation of this mixture on a distillation column (20 theoretical plates) at a reduced pressure affords a mixture of cis-LMO and trans-LMO (240 g) and 99% pure trans-isocarveol (376 g). Additional trans-isocarveol can be recovered from recycle fractions.

EXAMPLE 2

Preparation of Perillyl Alcohol from Trans-Isocarveol

A mixture of trans-isocarveol (99%, 680 g, prepared as described in Example A), ammonium metavanadate (1.05 g), and BHT (0.28 g) is agitated and heated at 160° C. for 10 h under a nitrogen atmosphere. The resulting mixture, which contains (by gas chromatography) trans-isocarveol (32%), cis-isocarveol (2.7%), and perillyl alcohol (64.2%), is washed with 5% aqueous sodium hydroxide solution (80 g) at 60° C. The organic phase is neutralized with acetic acid and fractionated on a distillation column (20 theoretical plates) at reduced pressure. Distillation gives trans-isocarveol (185 g) that can be reused and perillyl alcohol (99.9% pure, 398 g). The yield of perillyl alcohol based on reacted trans-isocarveol is 92%, including recycle cuts. Optical rotation: $[\alpha]_D^{22}=+104.5°$ (neat) when starting with LMO prepared from d-limonene.

EXAMPLES 3-7

Preparation of Perillyl Alcohol from Trans-Isocarveol

In each of Examples 3-7, a mixture of trans-isocarveol and ammonium metavanadate is agitated and heated at 160° C. for 10 h. As shown in Table 2, some examples include tert-butyl hydroquinone as an antioxidant, and some examples utilize a nitrogen atmosphere. The resulting mixture is washed with 5% aqueous sodium hydroxide solution as described earlier, and the organic phase is neutralized with acetic acid. The entire mixture is then quickly distilled at reduced pressure (1-2 mm Hg, 170° C. maximum pot temperature) on a short Vigreux column without fractionation, and the distillate is analyzed by gas chromatography to determine the content of cis- and trans-isocarveols and perillyl alcohol. The amount of undistilled residue is also measured. Results appear in Table 2.

TABLE 2

Conversion of trans-Isocarveol to Perillyl Alcohol

| Example # | 3 | 4 | 5 | 6 | 7 |
| --- | --- | --- | --- | --- | --- |
| trans-isocarveol, 97% (g) | 150 | 150 | 150 | 150 | 100 |
| ammonium metavanadate (g) | 0.23 | 0.23 | 0.23 | 0.23 | 0.20 |
| tert-butyl hydroquinone (g) | 0 | 0 | 0.06 | 0.06 | 0 |
| nitrogen atmosphere? | N | Y | N | Y | N |
| Distillate composition | | | | | |
| amount of distillate (g) | 136.6 | 138.3 | 136.1 | 139.8 | 85.0 |
| perillyl alcohol (%) | 59.8 | 56.5 | 61.6 | 56.6 | 58.9 |
| trans-isocarveol (%) | 33.3 | 38.0 | 31.6 | 38.1 | 26.4 |

TABLE 2-continued

Conversion of trans-Isocarveol to Perillyl Alcohol

| Example # | 3 | 4 | 5 | 6 | 7 |
| --- | --- | --- | --- | --- | --- |
| perillyl alcohol (g) | 81.7 | 78.1 | 83.8 | 79.1 | 50.1 |
| trans-isocarveol (g) | 45.5 | 52.6 | 43.0 | 53.3 | 22.4 |
| perillyl alcohol yield* (%) | 81.7 | 84.1 | 81.8 | 85.8 | 67.1 |
| residue (g) | 6.1 | 4.0 | 6.9 | 3.9 | 10.4 |
| residue (%, based on charged trans-isocarveol) | 4.07 | 2.67 | 4.60 | 2.60 | 10.4 |

*based on the amount of reacted trans-isocarveol

As shown in Table 2, good overall yields of perillyl alcohol are obtained in the direct isomerization process. Yields are somewhat higher when the reaction is performed under a nitrogen atmosphere (Exs. 4 and 6), particularly when TBHQ is also present (Ex. 6). The amount of residue is also reduced when a nitrogen atmosphere and TBHQ are used (compare Exs. 4 and 6 with Exs. 3 and 5) and when the amount of vanadium catalyst used is relatively low (compare Ex. 3 with Ex. 7).

EXAMPLE 8

High-Boiling Alcohol for Catalyst Recycle

A mixture of trans-isocarveol (150 g), ammonium vanadate (0.3 g), BHT (0.06 g), and triethylene glycol (22.5 g) is agitated and heated for 7 h at 160° C. under a nitrogen atmosphere. The resulting mixture is quickly distilled at reduced pressure (1-2 mm Hg, 145° C. maximum pot temperature) on a short Vigreux column without fractionation and the distillate is analyzed by gas chromatography. The crude distillate contains trans-isocarveol (34.1%), cis-isocarveol (2.9%), and perillyl alcohol (58.6%).

The residue from the above distillation, which contains vanadium catalyst solution in triethylene glycol, is reused three times to isomerize trans-isocarveol as follows. In each subsequent reaction, the recycle catalyst solution (residue after quick distillation), trans-isocarveol (150 g), and BHT (0.02 g) are agitated and heated for 7-10 h at 160° C. until the equilibrium between trans-isocarveol and perillyl alcohol is established. The resulting reaction mixture is then quickly distilled as described above. The distillates are combined for further fractionation, while the catalyst solution is reused for additional trans-isocarveol isomerizations.

The preceding examples are meant only as illustrations. The following claims define the invention.

We claim:
1. A process for making perillyl alcohol, comprising isomerizing a starting material comprising trans-isocarveol at a temperature within the range of 100° C. to 220° C. in the presence of a Group 5 metal catalyst to produce perillyl alcohol.
2. The process of claim 1 wherein the isomerization is performed at a temperature within the range of 130° C. to 190° C.
3. The process of claim 1 wherein the isomerization is performed under an inert atmosphere.
4. The process of claim 3 wherein the isomerization is performed under nitrogen.
5. The process of claim 1 wherein the isomerization is performed in the presence of a phenolic antioxidant.

6. The process of claim 5 wherein the phenolic antioxidant is 2,6-di-tert-butyl-4-methylphenol or tert-butyl hydroquinone.

7. The process of claim 1 wherein the catalyst is a salt, organic ester, or complex of a Group 5 metal.

8. The process of claim 1 wherein the catalyst comprises vanadium.

9. The process of claim 8 wherein the catalyst is ammonium metavanadate.

10. The process of claim 1 wherein the starting material further comprises cis-isocarveol.

11. The process of claim 1 further comprising recovering the perillyl alcohol by distillation.

12. The process of claim 11 wherein the distillation is performed in the presence of an alcohol having a boiling point greater than 260° C., and the resulting distillation residue is used to catalyze additional trans-isocarveol isomerizations.

13. The process of claim 12 wherein the alcohol is triethylene glycol.

14. The process of claim 1 wherein the perillyl alcohol has a neat optical rotation $[\alpha]_D^{22}$ of at least 104°.

* * * * *